United States Patent [19]

Hechenbleikner et al.

[11] Patent Number: 4,551,540

[45] Date of Patent: Nov. 5, 1985

[54] SUBSTITUTED 2,5-DIMETHYLPYRROLES

[75] Inventors: Ingenuin Hechenbleikner, West Cornwall; William P. Enlow, Falls Village, both of Conn.

[73] Assignee: Borg-Warner Chemicals, Inc., Parkersburg, W. Va.

[21] Appl. No.: 661,640

[22] Filed: Oct. 17, 1984

Related U.S. Application Data

[62] Division of Ser. No. 458,602, Jan. 17, 1983, abandoned.

[51] Int. Cl.$^4$ ............... C07D 207/327; C07D 207/36; C07D 207/30
[52] U.S. Cl. ................................ 548/531; 548/412; 548/536
[58] Field of Search ..................... 548/412, 531, 536

[56] References Cited

U.S. PATENT DOCUMENTS

| | | | |
|---|---|---|---|
| 2,453,672 | 11/1948 | Sargent | 548/536 |
| 2,453,677 | 11/1948 | Sickels | 548/536 |
| 2,479,971 | 8/1949 | Scholz | 548/531 |
| 2,527,165 | 10/1950 | Walker et al. | 548/536 |
| 3,060,194 | 10/1962 | Song et al. | 548/536 X |
| 3,083,208 | 3/1963 | Wu et al. | 548/536 X |
| 3,135,766 | 6/1964 | Gould | 548/536 X |
| 3,489,769 | 1/1970 | Helsley et al. | 548/536 X |
| 3,642,818 | 2/1972 | Rassat et al. | 548/536 |
| 3,816,452 | 6/1974 | Mrowca | 548/412 |
| 4,046,774 | 9/1977 | Napier | 548/412 |

OTHER PUBLICATIONS

Jones et al., "The Chemistry of Pyrroles", (1977), p. 77, Academic Press, (N.Y.).

McGraw-Hill: Dictionary of Scientific and Technical Terms, Lapedes-Editor, (1974), p. 87.

*Primary Examiner*—Joseph Paul Brust
*Attorney, Agent, or Firm*—Robert L. Zieg

[57] ABSTRACT

N-substituted 2,5-dimethylpyrroles and a method for their preparation. The method requires the reaction of a 2,5-hexadione such as acetonylacetone with a urethane or a phosphoroamidate. The reaction is carried out at elevated temperatures, preferably in a water-immiscible solvent.

8 Claims, No Drawings

SUBSTITUTED 2,5-DIMETHYLPYRROLES

This is a division of application Ser. No. 458,602 filed Jan. 17, 1983, now abandoned.

This invention relates as indicated to substituted 2,5-dimethylpyrroles and more particularly to a process for the preparation of such compounds.

BACKGROUND OF THE INVENTION

The substituted pyrroles of this invention are useful as intermediates in the syntheses of polymer additives which in turn are effective to protect various polymers from deterioration caused by exposure to ultraviolet light. The substituted pyrroles of the invention can be reacted with acetylene dicarboxylic acid, in a Diels-Alder reaction, for example, to form a much larger, less volatile compound which is effective to inhibit the deterioration of polypropylene upon exposure to ultraviolet light. This Diels-Alder product, containing an olefinic double bond, may be hydrogenated to yield a product which is an even more effective ultraviolet light stabilizer. Other active dienophiles may of course also be used for this purpose and illustrative examples include dialkyl maleates, alkyl acrylates and methacrylates, diethyl acetylene dicarboxylate, propargyl alcohol and butynediol.

The effectiveness of these Diels-Alder reaction products as light stabilizers is believed to be due to the hindered amide group.

Also, the acyl and phosphoryl groups may be removed (by hydrolysis) from these Diels-Alder condensation products and the resulting hindered amines likewise are effective ultraviolet light stabilizers in polymer compositions.

While a wide variety of polymers are benefitted by the protective action of these Diels-Alder products, olefin polymers are especially benefitted. Polypropylene, in particular, is susceptible to stabilization by the addition of a small proportion of such an additive.

The condensation of gamma-diketones such as hexane-2,5-dione, i.e., acetonylacetone, with primary amines to form pyrroles, is shown at page 77 of "The Chemistry of Pyrroles" by Jones et al., Academic Press (1977). The reaction is referred to as the Paal-Knorr condensation. It appears that the condensation reactions were carried out in aqueous systems because there is a considerable discussion about the optimum pH at which the reaction may be carried out. Moreover, it is stated that 2,5-dimethylpyrrole may be prepared from the reaction of hexane-2,5-dione and formamide; such a result was obtained in an aqueous environment.

SUMMARY OF THE INVENTION

The invention here is a substituted 2,5-dimethylpyrrole having the molecular structure

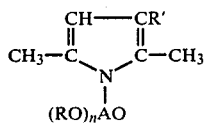

where R is alkyl or aralkyl and contains 1–19 carbon atoms, A is carbon or phosphorus, n is 1 or 2, and R' is hydrogen or carboalkoxy having 2–13 carbon atoms. The invention also includes a process for preparing such substituted 2,5-dimethylpyrroles comprising reacting acetonylacetone or a 3-carboalkoxyacetonylecetone with a urethane or phosphoramidate having the molecular structures, respectively,

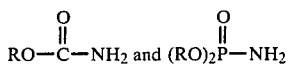

wherein R is alkyl or aralkyl of 1–19 carbon atoms. The process is illustrated by the following equations:

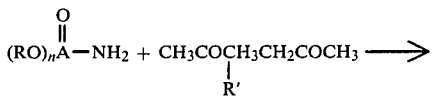

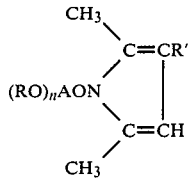

DETAILED DESCRIPTION OF THE INVENTION

R in the above structure may, as indicated, be alkyl or aryl. It may contain 1–19 carbon atoms. Illustrative examples of such R groups include methyl, ethyl, n-propyl, n-heptyl, n-nonyl, n-decyl, n-octadecyl, benzyl, beta-phenylethyl, etc.

Specific illustrative urethanes include aralkyl carbamates such as benzyl carbamate, alkyl carbamates such as methyl carbamate, ethyl carbamate and the like, as well as mixtures thereof, while the phosporamidates useful for the purposes of this invention include dialkylphosphoramidates such as diethylphosphoramidate, di-n-hexylphosphoramidate, etc.

It will be noted that the amide group of the composition of the invention is hindered by the two methyl groups in the 2- and 5- positions. It is believed that such hindrance is a factor in the notable effectiveness as light inhibitors of the Diels-Alder products which may be prepared from these substituted pyrroles.

The process of the invention is carried out in an anhydrous system. In some instances, to insure the substantial absence of water, it is advisable to heat, at reflux temperature, a solution of the amide in a water-immiscible solvent such as toluene, collecting any water in a Dean-Stark trap. Then when no more water is thus collected, acetonylacetone is added and the whole is heated until the reaction is complete.

The process requires the reaction of one mol of amide per one mol of acetonylacetone and, generally, these are the proportions of reactants that should be used for a most efficient reaction. The use of a substantial excess of either reactant merely results in the loss of the excessive amount of that reactant.

A catalyst ordinarily is used. Acidic catalysts are preferred. Illustrative examples of suitable acidic catalysts include p-toluenesulfonic acid, methanesulfonic acid, sulfonic acid, phosphoric acid, cationic resins such as sulfonated copolymers of butadiene and styrene, dilauryl phosphoric acid and the like.

It is desirable to use a solvent. Among other reasons, it faciliates removal of water, as it is formed, from the reaction mixture, viz., by means of a Dean-Stark trap.

Water-insoluble solvents should be used. Toluene, benzene, xylene, heptane, tetrachloroethane and chlorobenzene are illustrative. The boiling point of the solvent may range from about 75° C. to about 200° C., although a narrower range is preferred so as to permit easy removal (at a lower temperature) of the solvent from the product mixture, i.e., from about 100° C. to about 140° C.

The process is carried out quite simply; the reaction mixture is heated at a temperature within the range of from about 75° C. to about 200° C., usually at the reflux temperature of the solvent. Water is removed from the product mixture as it is formed and when no more water is formed the reaction is halted. The N-acyl-2,5-dimethylpyrrole product is isolated by distillation. The distillate usually comprises a mixture of the desired pyrrole and a small proportion of unreacted acetonylacetone. This latter can be removed by extraction with a solvent such as heptane; i.e., one which dissolves acetonylacetone more readily than the substituted pyrrole.

EXAMPLE 1

A solution of 55 g (0.364 mol) of benzyl carbamate, 42 ml. (40.4 g.–0.372 mol) of acetonylacetone and 0.25 g. of p-toluenesulfonic acid in 100 ml. of toluene is heated at reflux temperature for 7.5 hours, collecting evolved water in a Dean-Stark trap. A total of 13.5 ml. (0.75 mol) of water is thus collected. The product mixture is concentrated by heating to 130° C./5 mm. The residue is taken up in 100 ml. of heptane and filtered. The filtrate is concentrated to a purple solid, M.P. 62°–65° C., the desired carbobenzyloxy-2,5-dimethylpyrrole.

EXAMPLE 2

A solution of 10 g. (0.0653 mol) of diethyl phosphoramidate, 7.5 ml. (7.3 g.–0.0632 mol) of acetonylacetone and 0.1 g. of p-toluenesulfonic acid in 50 ml. of benzene is heated at reflux temperature. Evolved water is collected in a Dean-Stark trap. The residue is distilled at 90°–92°/0.1 mm. The distillate (shown below)

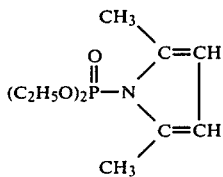

weighs 14.5 g.

EXAMPLE 3

A solution of 28. g. (0.246 mol) of acetonylacetone and 22 g. (0.247 mol) of ethyl carbamate in 50 ml. of ethanol is heated at reflux temperature for 1.5 hours. Gas chromatographic analysis indicates the formation of a small proportion of desired N-carboethoxy-2,5-dimethylpyrrole. The mixture is freed of ethanol by stripping, then heated at 150°–180° C. for six hours and distilled.

The distillate is shown by gas chromatographic analysis to be a mixture of starting materials and desired product. This mixture is dissolved in 50 ml. of carbon tetrachloride, 0.1 g. of p-toluenesulfonic acid is added, and the whole is heated at reflux temperature for ten hours during which period four ml. of water is collected in a Dean-Stark trap. The product mixture is distilled yielding two principal fractions of which the first fraction, weighing 30 g., was shown to contain mostly desired product and the second fraction, weighing 7 g., was shown to be substantially pure desired product, i.e., n-carboethyloxy-2,5-dimethylpyrrole.

It is apparent from this example that while the process of the invention can be carried out without an acidic catalyst, and without a water-immiscible solvent, it is carried out more efficiently when these two conditions obtain.

EXAMPLE 4

A solution of 70 g. (0.458 mol) of diethyl phosphoramidate, 52.5 ml (51.1 g.–0.449 mol) of acetonylacetone and 0.1 g. of p-toluenesulfonic acid in 200 ml. of benzene is heated at reflux temperature for several hours until a total of 15 ml. of water had been collected in a Dean-Stark trap. The product mixture is distilled into three fractions weighing 8.5 g. (B.P., <80° C./0.1 mm.), 71 g. (B.P. 80° C./0.1 mm.) and 15 g. (B.P. 82°–85° C. mm.), respectively. The middle fraction is shown by infrared analysis to be substantially pure substituted pyrrole of the following structure:

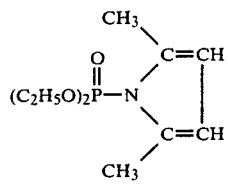

EXAMPLE 5

A solution of 28.0 g. (0.151 mol) of 3-carboethoxy-2,5-hexanediene, 13.4 g. (0.151 mol) of ethyl carbamate and 0.1 g. of p-toluenesulfonic acid in 100 ml. of heptane is heated at reflux temperature until a total of 5.0 g. of water is collected in a Dean-Stark trap. The product mixture is distilled yielding 15 g. of a fraction boiling at 115°–120° C./0.1 mm., $n_D^{20}$, 1.4897, and shown by gas chromatographic analysis to be the compound shown below:

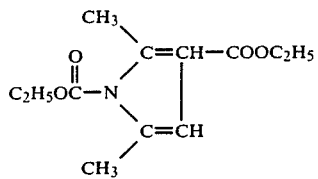

EXAMPLE 6

A solution of 114 g. (1.54 mols) of methyl carbamate, 180 ml. (175.3 g.–1.54 mols) of acetonylacetone and 0.1 g. of p-toluenesulfonic acid in 300 ml. of benzene is heated at reflux temperature until a total of 52 ml. of water is collected (in a Dean-Stark trap). The product mixture is stripped, then distilled yielding 208.5 of distillate which is identified as the desired N-carbomethoxy-2,5-dimethylpyrrole by means of infrared and gas chromatographic analysis.

All parts and percentages herein are by weight unless otherwise expressly stated.

We claim:

1. A substituted 2,5-dimethylpyrrole having the molecular structure:

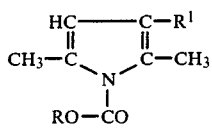

wherein R is alkyl or aralkyl and contains 1–19 carbon atoms, and $R^1$ is hydrogen or carboalkoxy having 2–5 carbon atoms.

2. The substituted 2,5-dimethylpyrrole of claim 1 wherein R is alkyl.

3. The substituted 2,5-dimethylpyrrole of claim 1 wherein R is alkyl of 1–4 carbon atoms.

4. The substituted 2,5-dimethylpyrrole of claim 1 wherein $R^1$ is hydrogen.

5. A process for preparing substituted 2,5-dimethylpyrroles having the molecular structure:

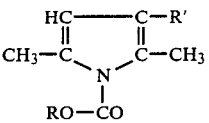

wherein R is alkyl or aralkyl and contains 1–19 carbon atoms, R' is hydrogen or carboalkoxy having 2–5 carbon atoms, said process comprising reacting acetonylacetone or a 3-carboalkoxy acetonylacetone with a urethane having the molecular structure:

$ROCONH_2$ wherein R is alkyl or aralkyl of 1–19 carbon atoms in a water-immiscible solvent at a temperature of between 75° and 200° C. in the presence of an acidic catalyst, removing water and isolating the said substituted 2,5-dimethylpyrrole.

6. The process of claim 5 wherein R is alkyl.

7. The substituted 2,5-dimethylpyrrole of claim 1 wherein R is selected from the group consisting of benzyl, ethyl and methyl.

8. The process of claim 5 wherein R is selected from the group consisting of benzyl, ethyl and methyl.

* * * * *